(12) United States Patent
Pate et al.

(10) Patent No.: US 12,295,645 B2
(45) Date of Patent: May 13, 2025

(54) SYSTEMS AND METHODS FOR ADHERING VESSELS

(71) Applicant: TVA Medical, Inc., Austin, TX (US)

(72) Inventors: Thomas D. Pate, Austin, TX (US); Philip M. Tetzlaff, Austin, TX (US); William E. Cohn, Bellaire, TX (US)

(73) Assignee: TVA Medical, Inc., Franklin Lakes, NJ (US)

(*) Notice: Subject to any disclaimer, the term of this patent is extended or adjusted under 35 U.S.C. 154(b) by 687 days.

(21) Appl. No.: 16/024,241

(22) Filed: Jun. 29, 2018

(65) Prior Publication Data

US 2019/0133678 A1 May 9, 2019

Related U.S. Application Data

(63) Continuation of application No. PCT/US2017/013611, filed on Jan. 15, 2017.
(Continued)

(51) Int. Cl.
*A61B 18/14* (2006.01)
*A61B 17/11* (2006.01)
(Continued)

(52) U.S. Cl.
CPC .......... *A61B 18/1492* (2013.01); *A61B 17/11* (2013.01); *A61B 18/082* (2013.01);
(Continued)

(58) Field of Classification Search
CPC ..... A61B 18/1492; A61B 18/10; A61B 34/73; A61B 18/16; A61B 17/11; A61B 18/082; A61B 2018/00702; A61B 2017/00477; A61B 2018/00077; A61B 2018/00273; A61B 17/320068; A61B 18/24;
(Continued)

(56) References Cited

U.S. PATENT DOCUMENTS 3,649,850 A 3/1972 Davis
3,827,436 A 8/1974 Stumpf et al.
(Continued)

FOREIGN PATENT DOCUMENTS

CA 2883209 A1 4/2014
CN 1730123 A 2/2006
(Continued)

OTHER PUBLICATIONS

International Search Report and Written Opinion pertaining to PCT/US2019/034896, mailed May 12, 2020.
(Continued)

*Primary Examiner* — Linda C Dvorak
*Assistant Examiner* — Nicholas S Borsch
(74) *Attorney, Agent, or Firm* — Dickinson Wright PLLC; Andrew D. Dorisio

(57) ABSTRACT

Described here are devices, systems, and methods for adhering tubular structures, such as blood vessels. Generally, the methods may comprise advancing a first catheter comprising a first adhesion element into a first blood vessel and a second catheter comprising a second adhesion element into a second blood vessel. The vessels may be adhered together by heating tissue using the first and second adhesion elements.

16 Claims, 13 Drawing Sheets

Related U.S. Application Data

(60) Provisional application No. 62/279,642, filed on Jan. 15, 2016.

(51) Int. Cl.
*A61B 18/08* (2006.01)
*A61B 18/10* (2006.01)
*A61B 18/16* (2006.01)
*A61B 34/00* (2016.01)
*A61B 17/00* (2006.01)
*A61B 17/32* (2006.01)
*A61B 18/00* (2006.01)
*A61B 18/24* (2006.01)

(52) U.S. Cl.
CPC .............. *A61B 18/10* (2013.01); *A61B 18/16* (2013.01); *A61B 34/73* (2016.02); *A61B 2017/00402* (2013.01); *A61B 2017/00477* (2013.01); *A61B 2017/00876* (2013.01); *A61B 2017/1107* (2013.01); *A61B 2017/1139* (2013.01); *A61B 17/320068* (2013.01); *A61B 2018/00077* (2013.01); *A61B 2018/00136* (2013.01); *A61B 2018/00273* (2013.01); *A61B 2018/00404* (2013.01); *A61B 2018/00589* (2013.01); *A61B 2018/00601* (2013.01); *A61B 2018/00619* (2013.01); *A61B 2018/00702* (2013.01); *A61B 2018/00791* (2013.01); *A61B 2018/00875* (2013.01); *A61B 18/24* (2013.01)

(58) Field of Classification Search
CPC ........... A61B 2017/00402; A61B 2018/00136; A61B 2018/00589; A61B 2018/00601; A61B 2017/00876; A61B 2017/1107; A61B 2017/1139; A61B 2018/00404; A61B 2018/00619; A61B 2018/00791; A61B 2018/00875; A61B 2090/376
See application file for complete search history.

(56) References Cited

U.S. PATENT DOCUMENTS

| | | | |
|---|---|---|---|
| 4,416,664 A | 11/1983 | Womack | |
| 4,802,475 A | 2/1989 | Weshahy | |
| 5,313,943 A | 5/1994 | Houser et al. | |
| 5,383,460 A | 1/1995 | Jang et al. | |
| 5,429,131 A * | 7/1995 | Scheinman ............ | A61B 5/287 600/509 |
| 5,697,909 A | 12/1997 | Eggers et al. | |
| 5,782,239 A | 7/1998 | Webster, Jr. | |
| 5,800,487 A | 9/1998 | Mikus et al. | |
| 5,830,222 A | 11/1998 | Makower | |
| 5,830,224 A | 11/1998 | Cohn et al. | |
| 5,836,947 A | 11/1998 | Fleischman et al. | |
| 5,895,404 A | 4/1999 | Ruiz | |
| 5,971,979 A | 10/1999 | Joye et al. | |
| 6,004,330 A | 12/1999 | Middleman et al. | |
| 6,032,677 A | 3/2000 | Blechman et al. | |
| 6,039,730 A | 3/2000 | Rabin et al. | |
| 6,068,638 A | 5/2000 | Makower | |
| 6,071,274 A | 6/2000 | Thompson et al. | |
| 6,099,542 A | 8/2000 | Cohn et al. | |
| 6,159,225 A | 12/2000 | Makower | |
| 6,190,353 B1 | 2/2001 | Makower et al. | |
| 6,197,025 B1 | 3/2001 | Grossi et al. | |
| 6,217,575 B1 | 4/2001 | DeVore et al. | |
| 6,231,587 B1 | 5/2001 | Makower | |
| 6,256,525 B1 | 7/2001 | Yang et al. | |
| 6,280,440 B1 * | 8/2001 | Gocho ............... | A61B 18/1492 606/49 |
| 6,283,988 B1 | 9/2001 | Laufer et al. | |
| 6,287,306 B1 | 9/2001 | Kroll et al. | |
| 6,302,875 B1 | 10/2001 | Makower et al. | |
| 6,327,505 B1 | 12/2001 | Medhkour et al. | |
| 6,347,247 B1 | 2/2002 | Dev et al. | |
| 6,355,029 B1 | 3/2002 | Joye et al. | |
| 6,357,447 B1 | 3/2002 | Swanson et al. | |
| 6,379,353 B1 | 4/2002 | Nichols | |
| 6,383,180 B1 | 5/2002 | Lalonde et al. | |
| 6,394,956 B1 | 5/2002 | Chandrasekaran et al. | |
| 6,400,976 B1 | 6/2002 | Champeau | |
| 6,428,534 B1 | 8/2002 | Joye et al. | |
| 6,461,356 B1 | 10/2002 | Patterson | |
| 6,464,665 B1 | 10/2002 | Heuser | |
| 6,464,723 B1 | 10/2002 | Callol | |
| 6,468,268 B1 | 10/2002 | Abboud et al. | |
| 6,475,214 B1 | 11/2002 | Moaddeb | |
| 6,475,226 B1 | 11/2002 | Belef et al. | |
| 6,527,724 B1 | 3/2003 | Fenici | |
| 6,527,769 B2 | 3/2003 | Langberg et al. | |
| 6,542,766 B2 | 4/2003 | Hall et al. | |
| 6,544,230 B1 | 4/2003 | Flaherty et al. | |
| 6,569,158 B1 | 5/2003 | Abboud et al. | |
| 6,569,162 B2 | 5/2003 | He | |
| 6,579,311 B1 | 6/2003 | Makower | |
| 6,585,650 B1 | 7/2003 | Solem | |
| 6,592,577 B2 | 7/2003 | Abboud et al. | |
| 6,629,987 B1 | 10/2003 | Gambale et al. | |
| 6,635,053 B1 | 10/2003 | Lalonde et al. | |
| 6,655,386 B1 | 12/2003 | Makower et al. | |
| 6,656,173 B1 | 12/2003 | Palermo | |
| 6,663,625 B1 | 12/2003 | Ormsby et al. | |
| 6,669,709 B1 | 12/2003 | Cohn et al. | |
| 6,673,085 B1 | 1/2004 | Berg | |
| 6,676,657 B2 | 1/2004 | Wood | |
| 6,682,525 B2 | 1/2004 | Lalonde et al. | |
| 6,695,878 B2 | 2/2004 | McGuckin et al. | |
| 6,709,444 B1 | 3/2004 | Makower | |
| 6,719,756 B1 | 4/2004 | Muntermann | |
| 6,726,697 B2 | 4/2004 | Nicholas et al. | |
| 6,733,494 B2 | 5/2004 | Abboud et al. | |
| 6,736,808 B1 | 5/2004 | Motamedi et al. | |
| 6,761,708 B1 | 7/2004 | Chiu et al. | |
| 6,761,714 B2 | 7/2004 | Abboud et al. | |
| 6,780,181 B2 | 8/2004 | Kroll et al. | |
| 6,849,073 B2 | 2/2005 | Hoey et al. | |
| 6,855,143 B2 | 2/2005 | Davison et al. | |
| 6,887,234 B2 | 5/2005 | Abboud et al. | |
| 6,911,026 B1 | 6/2005 | Hall et al. | |
| 6,932,814 B2 | 8/2005 | Wood | |
| 6,936,024 B1 | 8/2005 | Houser | |
| 6,960,209 B2 | 11/2005 | Clague et al. | |
| 6,971,983 B1 | 12/2005 | Cancio | |
| 6,981,972 B1 | 1/2006 | Farley et al. | |
| 7,059,330 B1 | 6/2006 | Makower et al. | |
| 7,060,063 B2 | 6/2006 | Marion et al. | |
| 7,094,235 B2 | 8/2006 | Francischelli | |
| 7,155,293 B2 | 12/2006 | Westlund et al. | |
| 7,179,270 B2 | 2/2007 | Makower | |
| 7,189,231 B2 | 3/2007 | Clague et al. | |
| 7,214,234 B2 | 5/2007 | Rapacki et al. | |
| 7,231,260 B2 | 6/2007 | Wallace et al. | |
| 7,250,051 B2 | 7/2007 | Francischelli | |
| 7,288,075 B2 | 10/2007 | Parihar et al. | |
| 7,303,554 B2 | 12/2007 | Lalonde et al. | |
| 7,306,598 B2 | 12/2007 | Truckai et al. | |
| 7,335,198 B2 | 2/2008 | Eggers et al. | |
| 7,341,063 B2 | 3/2008 | Garbibaldi et al. | |
| 7,367,341 B2 | 5/2008 | Anderson et al. | |
| 7,374,567 B2 | 5/2008 | Heuser | |
| 7,387,636 B2 | 6/2008 | Cohn et al. | |
| 7,407,506 B2 | 8/2008 | Makower | |
| 7,522,950 B2 | 4/2009 | Fuimaono et al. | |
| 7,628,768 B2 | 12/2009 | Faul et al. | |
| 7,702,387 B2 | 4/2010 | Stevenson et al. | |
| 7,727,268 B2 | 6/2010 | Cunniffe et al. | |
| 7,744,596 B2 | 6/2010 | Young et al. | |
| 7,811,281 B1 | 10/2010 | Rentrop | |
| 7,828,814 B2 | 11/2010 | Brenneman et al. | |
| 7,846,172 B2 | 12/2010 | Makower | |
| 7,849,860 B2 | 12/2010 | Makower et al. | |

(56) References Cited

U.S. PATENT DOCUMENTS

| | | |
|---|---|---|
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| RE43,007 E | 12/2011 | Lalonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,510,901 B2 | 12/2016 | Steinke et al. |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Peña et al. |
| 10,596,356 B2 | 3/2020 | Lenihan et al. |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0098095 A1 | 5/2004 | Burnside et al. |
| 2004/0167506 A1* | 8/2004 | Chen ............... A61B 18/04 606/27 |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0039830 A1* | 2/2008 | Munger ............ A61B 18/1492 606/33 |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1* | 5/2008 | Brenneman ........ A61B 17/3468 206/363 |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0221519 A1 | 9/2008 | Schwach et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty |
| 2009/0157014 A1 | 6/2009 | Osborne et al. |
| 2009/0187098 A1 | 7/2009 | Makower et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2010/0318180 A1 | 12/2010 | Porter |
| 2011/0015657 A1 | 1/2011 | Brenneman et al. |

(56) References Cited

U.S. PATENT DOCUMENTS

| | | |
|---|---|---|
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman |
| 2011/0306993 A1* | 12/2011 | Hull .................... A61N 7/02 606/151 |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | MacHold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1* | 11/2012 | Miller ............ A61B 17/320016 604/8 |
| 2013/0041306 A1 | 2/2013 | Faul et al. |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2013/0296704 A1 | 11/2013 | Magnin et al. |
| 2014/0012251 A1 | 1/2014 | Himmelstein et al. |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1* | 2/2015 | Gittard ................ A61B 17/11 606/153 |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0126965 A1 | 5/2015 | Liungman |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196309 A1 | 7/2015 | Matsubara et al. |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0051323 A1 | 2/2016 | Stigall et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0100840 A1 | 4/2016 | Brenneman et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1 | 7/2016 | Dickinson et al. |
| 2017/0071627 A1 | 3/2017 | Kellerman et al. |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2017/0232272 A1 | 8/2017 | Perkins et al. |
| 2017/0252006 A1 | 9/2017 | Tsuruno |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0038103 A1 | 2/2020 | Pappone et al. |
| 2020/0061338 A1 | 2/2020 | Pate |
| 2020/0178970 A1 | 6/2020 | Berman et al. |

FOREIGN PATENT DOCUMENTS

| | | | |
|---|---|---|---|
| CN | 101730557 A | 6/2010 | |
| EP | 0923912 A2 | 6/1999 | |
| JP | 11514269 A | 12/1999 | |
| JP | 3127126 | 11/2006 | |
| JP | 2009545338 A | 12/2009 | |
| JP | 2014500072 A | 1/2014 | |
| RU | 2168951 C1 | 6/2001 | |
| WO | 9713463 W | 4/1997 | |
| WO | 9729682 A1 | 8/1997 | |
| WO | 9956640 A1 | 11/1999 | |
| WO | 2006105008 A1 | 10/2006 | |
| WO | 2008010039 A2 | 1/2008 | |
| WO | 2009005644 A2 | 1/2009 | |
| WO | 2011100625 A2 | 8/2011 | |
| WO | 2012068273 A1 | 5/2012 | |
| WO | WO-2013112584 A1 * | 8/2013 | ......... A61B 18/1492 |
| WO | 2014028306 A1 | 2/2014 | |
| WO | 2014052919 A1 | 4/2014 | |
| WO | 2015061614 A1 | 4/2015 | |
| WO | 2015085119 A1 | 6/2015 | |
| WO | 2015108984 A1 | 7/2015 | |
| WO | 2016033380 A1 | 3/2016 | |
| WO | 2016081321 A2 | 5/2016 | |
| WO | 2017124059 A1 | 7/2017 | |
| WO | 2017124060 A1 | 7/2017 | |
| WO | 2018057095 A1 | 3/2018 | |

OTHER PUBLICATIONS

Maybury et al., "The Effect of Roll Angle on the Performance of Halbach Arrays," University of California-San Diego, Center for Magnetic Recording Research (2008), 19 pgs.

Choi, et al., Design of a Halbach Magnet Array Based on Optimization Techniques; IEEE Transactions on Magnetics, vol. 44, No. 10, Oct. 2008, pp. 2361-2366. (Year: 2008).

"Banasik et al. (2011)." "A rare variant route of the ulnar artery does not contraindicate the creation of a fistula in the wrist of a diabetic patient with end-stage renal disease," "Postepy Hig Med Dosw. 65:654-657."

Bharat et al. (2012). "A novel technique of vascular anastomosis to prevent juxta-anastomotic stenosis following arteriovenous fistula creation," J. Vascular Surgery 55(1):274-280.

Bode et al. (2011 ). "Clinical study protocol for the arch project Computational modeling for improvement of outcome after vascular access creation," J. Vasc. Access 12(4):369-376.

Hakim et al., "Ulnar artery-based free forearm flap: Review of Specific anatomic features in 322 cases and related literature," Heand & Neck, Dec. 2013 (published online:2014), Wiley Online Library.

(56) References Cited

OTHER PUBLICATIONS

Davidson, I. et al. (2008). "Duplex Ultrasound Evaluation for Dialysis Access Selection and Maintenance: A Practical Guide," The Journal of Vascular Access 9(1): 1-9.
Gracz, et al. (1977). "Proximal forearm fistula for maintenance hemodialysis," Kidney International 11:71-75.
Jennings, WC. et al. (2011). "Primary arteriovenous fistula inflow proximalization for patients at high risk for dialysis access-associated ischemic steal syndrome," J. Vasc. Surgery 54(2):554-558.
Kinnaert, et al. (1971). "Ulnar Arteriovenous Fistula for Maintenance Haemodial Ysis," British J. Surgery 58(9):641-643.
Morale et al. (2011). "Venae comitantes as a potential vascular resource to create native arteriovenous fistulae," J. Vasc. Access 12(3):211-214.
Shenoy, S. (2009). "Surgical anatomy of upper arm: what is needed for AVF planning," The Journal of Vascular Access 10:223-232.
Vachharajani, T. (2010). "Atlas of Dialysis Vascular Access," Wake Forest University School of Medicine, 77 total pages.
Whittaker et al. (2011). "Prevention better than cure. Avoiding steal syndrome with proximal radial or ulnar arteriovenous fistulae" J. Vasc. Access 12(4):318-320.
Office Action pertaining to corresponding Japanese Patent Application No. 2018-536423, dated Feb. 12, 2021.
Extended European Search Report pertaining to EP Patent Application No. 17853586.0, dated Apr. 29, 2020.
Extended European Search Report for EP Application No. 17739123.2.
Office Action dated Jun. 4, 2021, pertaining to Japanese Patent Application No. 2019-516190.
Office Action dated Dec. 23, 2022, pertaining to Chinese Patent Application No. 201780017044.7.
Office Action, dated Feb. 9, 2023, pertaining to Brazil Patent Application No. BR112018014010-4.

* cited by examiner

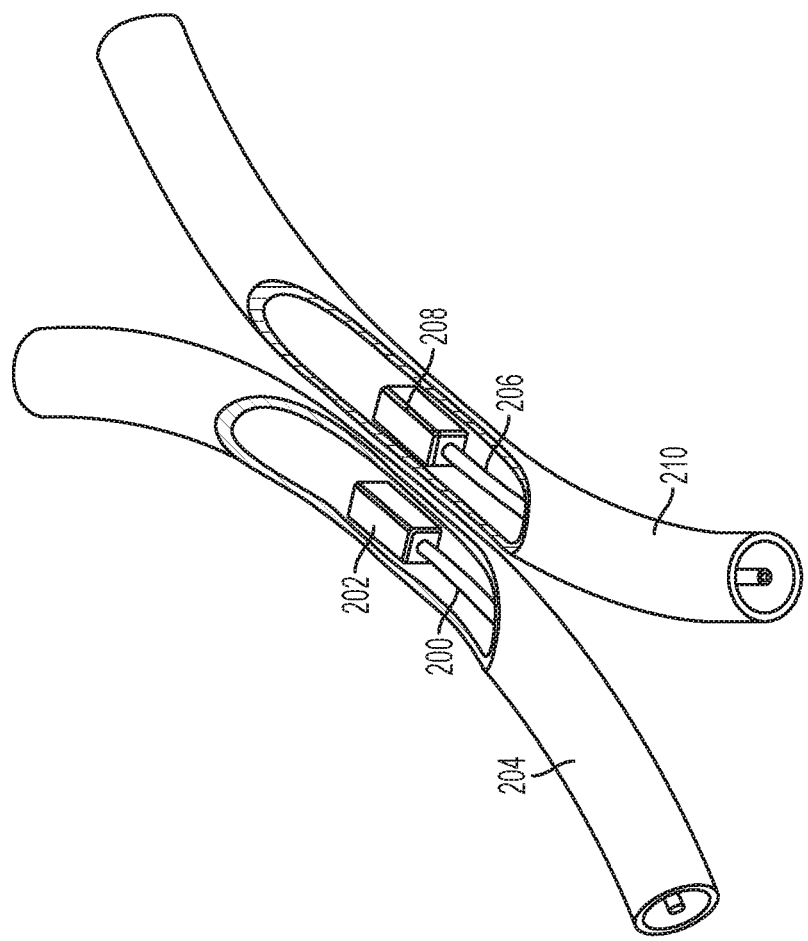
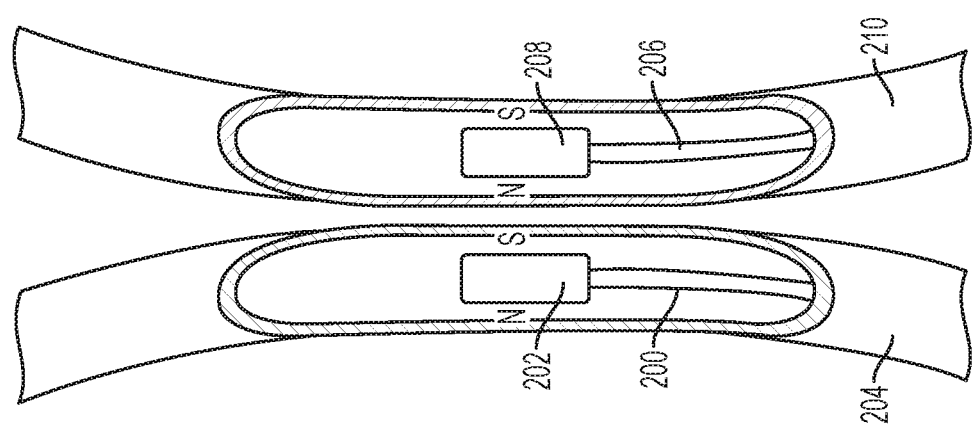
FIG. 2B
FIG. 2A

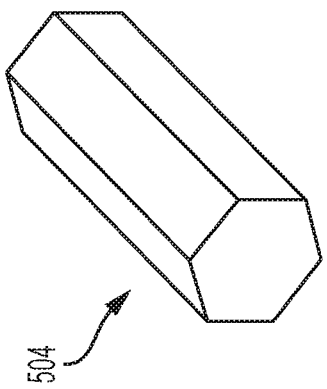
FIG. 5C
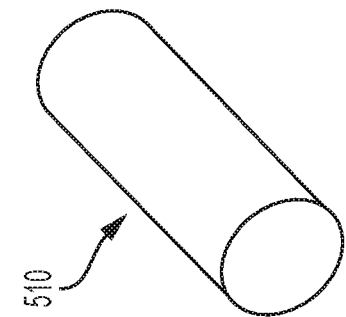
FIG. 5F
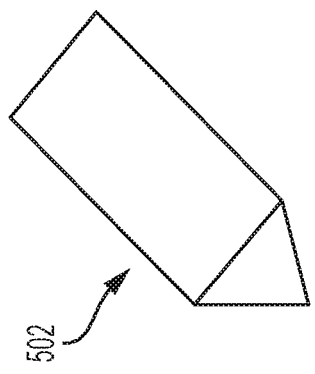
FIG. 5B
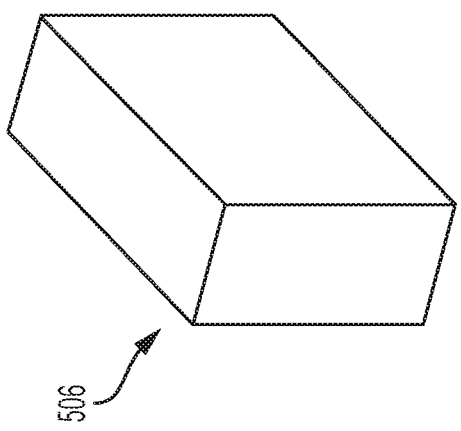
FIG. 5E
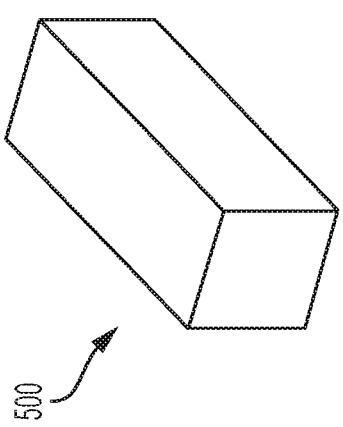
FIG. 5A
FIG. 5D

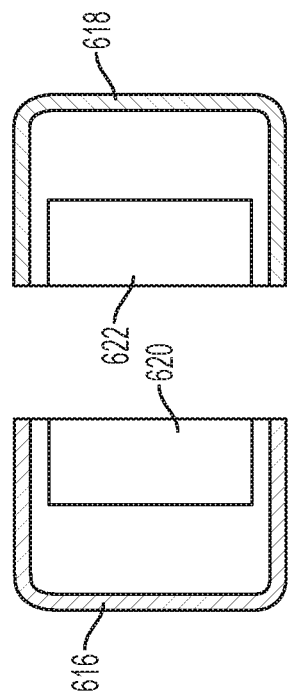
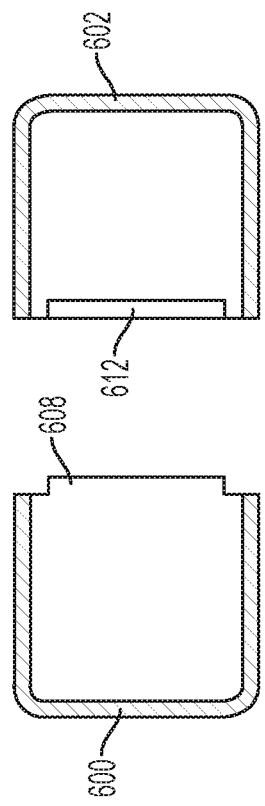
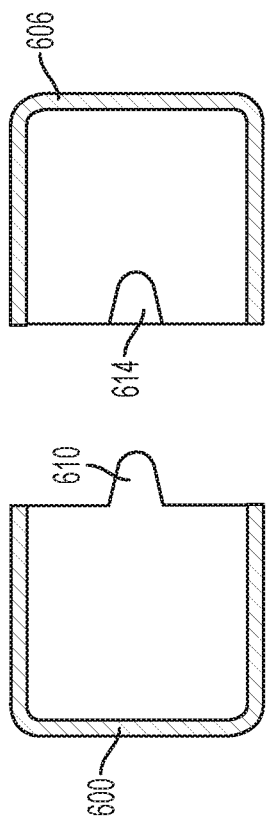

SYSTEMS AND METHODS FOR ADHERING VESSELS

CROSS-REFERENCE TO RELATED APPLICATIONS

This application is a continuation of International Application No. PCT/US2017/013611, filed Jan. 15, 2017, which claims the benefit of U.S. Provisional Application No. 62/279,642, filed Jan. 15, 2016, and titled "SYSTEMS AND METHODS FOR ADHERING VESSELS," each of which is hereby incorporated by reference in its entirety.

FIELD

The current invention relates to systems and methods for adhering tubular structures within the body, such as vessels.

BACKGROUND

The devices, systems, and methods described here may be used to enhance mechanical adhesion between tubular structures within the body. In some instances, this may be desirable to improve mechanical adhesion between tubular structures used to form fistulas. A fistula is generally a passageway formed between two internal organs. Forming a fistula between two tubular structures, such as blood vessels, can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Generally, fistula formation requires surgical dissection of a target vein, and transecting and moving the vein for surgical anastomosis to the artery. It may therefore be useful to find improved ways to form a fistula between two blood vessels.

BRIEF SUMMARY

Described here are devices, systems, and methods for adhering two or more tubular structures together. The tubular structures may be any suitable tubular structure, such as an artery, vein, duct, digestive tract, and so forth. For example, the devices, systems, and methods disclosed herein may increase mechanical adhesion between two blood vessels such as an artery and a vein, a vein and a vein, an artery and an artery, or between a duct and a duct, a digestive tract and a digestive tract, and the like.

Generally, a method for adhering tubular structures described herein comprises advancing a first catheter into a first tubular structure and a second catheter into a second tubular structure. The first catheter may comprise a first adhesion element and the second catheter may comprise a second adhesion element. The first adhesion element may be aligned with the second adhesion element. The first and second tubular structures may be adhered by heating tissue between the two adhesion elements.

In some variations, a method of adhering vessels together comprises advancing a first catheter comprising a first magnetic adhesion element into a first blood vessel and a second catheter comprising a second magnetic adhesion element into a second blood vessel. The first magnetic adhesion element may be aligned with the second magnetic adhesion element. In some variations, the first magnetic adhesion element may be aligned with the second magnetic adhesion element by fluoroscopically visualizing at least a portion of the first and second catheters. In some variations, the first and/or second catheters may comprise one or more rotational indicators. The rotational indicators may be fluoroscopically visualized to align the catheters. Tissue of the first and second blood vessels may be compressed between the first and second magnetic adhesion elements. An adhesion (weld) may be formed between the first blood vessel to the second blood vessel by using the magnetic adhesion elements to heat tissue of the first and second blood vessels between the magnetic adhesion elements. In some variations, the tissue may be heated by delivery of radiofrequency energy from the magnetic adhesion elements. In other variations, the tissue may be heated by ohmic heating of the magnetic adhesion elements. In these variations the magnetic adhesion elements may comprise a resistor. Heating may occur over a single cycle, or a plurality of cycles. In some variations, impedance between the magnetic adhesion elements may be monitored before, after, or during energy delivery. Additionally or alternatively, tissue temperature may be monitored before, after, or during energy delivery. In some variations, a second adhesion may be formed between the first blood vessel and the second blood vessel. The formed adhesion(s) may in some instances have a width between about 0.1 mm and about 15 mm, and a length between about 0.1 mm and about 10 cm. In some variations, a fistula may be formed through the adhesion. For example, a fistula may be formed through the adhesion using the magnetic adhesion elements.

In some variations, a system for adhering two tubular structures together comprises a first catheter comprising a first adhesion element and a second catheter comprising a second adhesion element. The first adhesion element may be magnetic and may comprise a flat contact surface. The second adhesion element may be magnetic and comprise a flat contact surface. A power source may be connected to the first and second adhesion elements. In some variations, the first adhesion element may be located at a distal end of the first catheter, and the second adhesion element may be located at a distal end of the second catheter. The first and/or second adhesion elements may be coated with one or more layers of a fluoropolymer. Additionally or alternatively, the first and/or second magnetic adhesion elements may comprise surface insulation. In some variations, the first adhesion element may define a recess. In some of these variations, the second adhesion element may comprise a protrusion complementary to the recess. In some variations, the first and/or second catheter may comprise a rotational indicator.

In some variations, the first catheter may comprise a proximal portion and a distal portion, wherein the largest cross-sectional dimension of the distal portion is larger than the largest cross-sectional dimension of the proximal portion. The first adhesion element may be located on the distal portion. Additionally or alternatively, the second catheter may comprise a proximal portion and a distal portion, wherein the largest cross-sectional dimension of the distal portion is larger than the largest cross-sectional dimension of the proximal portion. The second adhesion element may be located on the distal portion. In some variations, at least one of the pushability, flexibility, or torquability of the first and/or second catheter may be adjustable. For example, the first catheter may comprise a distal portion, an inner proximal portion, and an outer proximal portion. The outer proximal portion may be slidable relative to the distal portion. The distal portion may have a retracted configuration and an extended configuration. The distal portion may be configured to extend away from the outer proximal portion when moved from the retracted configuration to the extended configuration.

BRIEF DESCRIPTION OF THE DRAWINGS

FIGS. 2A-2D are views of an illustrative system described here in vasculature.

FIGS. 5A-5F are perspective views of variations of adhesion elements.

FIGS. 6A-6C are cross-sectional side views of variations of adhesion elements.

DETAILED DESCRIPTION

Figure 1:
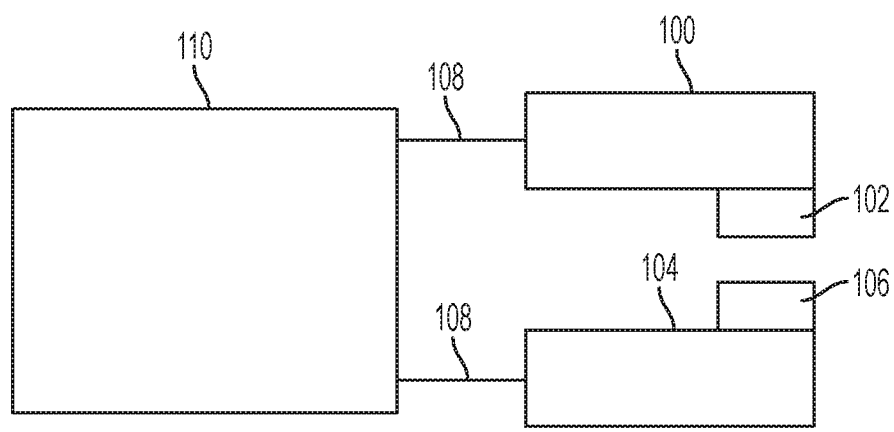
FIG. 1 is a block diagram of an illustrative variation of a system.

Generally described here are devices, systems, and methods for increasing mechanical adhesion between tubular structures, such as blood vessels, and in some instances forming a weld between the structures to adhere the two structures together. Generally, to adhere two tubular structures together, a system comprising multiple catheters may be advanced in a minimally invasive fashion (e.g., for blood vessels, via the vasculature) to a target location and used to adhere the tubular structures together. In some examples, the tubular structures may comprise blood vessels such as two arteries, two veins, or a vein and an artery.

Generally, each catheter may comprise an adhesion element. An adhesion element may comprise an element capable of adhering tissue, either alone or in combination with another adhesion element. An adhesion element may be configured to adhere tissue together by heating the tissue. In some variations, an adhesion element may heat issue by delivering electrical energy to the tissue. In some of these variations, the adhesion element may comprise a magnet configured to heat tissue by delivering electrical current, as described in more detail herein. In other variations, an adhesion element may be heated through resistive heating, which may in turn heat tissue. In yet other variations, an adhesion element may heat tissue using laser energy. For example, a catheter may comprise a fiber optic filament coupled to a laser, such that the adhesion element may be configured to direct laser energy to heat tissue. In yet another variation, an adhesion element may deliver ultrasonic energy to heat tissue. In such a variation, the adhesion element may comprise a piezoelectric element configured to use ultrasonic vibration to induce heating.

A first catheter comprising an adhesion element may be placed at a target location in a first tubular structure, and a second catheter comprising an adhesion element may be placed at a target location in a second tubular structure. The catheters may be aligned relative to each other using the adhesion elements, coaption regions, and/or visual alignment aids, as described in more detail herein. For example, when the tubular structures are blood vessels, a first catheter may be placed in a first blood vessel, and a second catheter may be placed in a second blood vessel, where the first and second vessels are in proximity to each other, and the two catheters may be aligned to coapt the two vessels. Tissue heating due to one or more adhesion elements may adhere tissue of the first tubular structure to tissue of the second tubular structure. For example, current applied to blood vessel walls may denature proteins in each vessel, which may cause them to adhere together. Adhesion may be performed before, during, or after other procedures, such as fistula formation, as described in more detail herein.

I. Systems

Generally, the systems described here are configured to adhere tubular structures in the body, such as blood vessels. In some variations, the systems comprise two catheters each comprising one or more adhesion elements. An adhesion element may comprise an element capable of adhering tissue, either alone or in combination with another adhesion element, and may be configured to adhere tissue together by heating the tissue. In some variations, an adhesion element may heat issue by delivering electrical current to the tissue, while in other variations an adhesion element may heat tissue by delivering laser or ultrasonic energy to the tissue. In yet other variations, an adhesion element may be resistively heated, which may in turn heat tissue. In some variations, an adhesion element may comprise a magnet configured to deliver energy to tissue, although in other variations it may comprise a non-magnetic element.

The adhesion elements may be configured to be delivered to target locations in tubular structures (e.g., blood vessels) via catheters. When an adhesion element is configured to heat tissue by delivering electrical energy, it may comprise a contact surface configured to contact tissue (e.g., a blood vessel wall) or fluid (e.g., blood). When the contact surface is in contact with tissue and/or fluid at the target location, it may supply current to and/or carry current from the tissue and/or fluid. This may result in heat, which in turn may facilitate adhesion of one portion of tissue to another. More particularly, current applied to the adhesion elements may be configured to heat and/or desiccate tissue to mechanically adhere the vessels together through protein denaturation. In some instances, tissue may be thermally welded together by applying a coagulation current to an electrode to denature connective tissue proteins and thereby increase adhesion between tissue planes. In some instances, the denatured proteins from each vessel may intertwine to fuse together and/or shrink the vessel. In some variations, thermal denaturing and welding may modify the vessel without removing material as occurs when ablating tissue.

FIG. 1 is a block diagram of one variation of a system comprising a first catheter (100) and a second catheter (104). The first catheter (100) may comprise a first adhesion element (102) and the second catheter (104) may comprise a second adhesion element (106). At least a portion of the adhesion elements may be exposed to the surrounding environment (i.e., may not be fully encompassed by the catheters). The adhesion elements (102, 106) may comprise electrically conductive magnets, as described in more detail herein, although they need not be magnetic. In use, the first catheter (100) and the second catheter (104) may be placed in first and second tubular structures (e.g., blood vessels), respectively, wherein the tubular structures are adjacent, and the adhesion elements (102, 106) may interact to adhere the outer wall of the first structure (e.g., blood vessel) to the outer wall of the second structure (e.g., blood vessel). In some variations, the adhesion elements may adhere the tissue by delivering electrical energy to the tissue. As such, a proximal end of each catheter (100, 104) may be connected to a power supply (110) by respective connections (108). The power supply (110) may further comprise a controller (not shown) for controlling energy delivery to the catheters (100, 104). The power supply (110) may be an AC or DC power supply. The power supply (110) may output current to heat and/or desiccate tissue.

In some variations, the adhesion elements (102, 106) may each deliver electrical energy to heat tissue. For example, each adhesion elements (102, 106) may be connected to an active output of the power supply (110) to deliver current and thus heat adjacent tissue. As such, the adhesion elements (102, 106) may simultaneously heat tissue from opposing sides. A ground pad (e.g., a large metal plate or flexible metalized pad) affixed to the patient may be connected to a return terminal of the power supply. In other variations, the first adhesion element (102) may be connected to the active output of the power supply (110) and the second adhesion element (106) may be connected to the return terminal. In yet other variations, the first adhesion element (102) may be connected to an output of the power supply, and the second adhesion element (106) may be floating, that is, not directly connected to any output of the power supply, in a focused monopolar configuration.

It should be appreciated that in other variations, only the first catheter may be connected to the power supply in a monopolar configuration. For example, only the first adhesion element may heat tissue, while the second adhesion element may mechanically contribute to tissue adhesion by pressing tissue toward the first adhesion element while the first adhesion element heats tissue. In such a configuration, the first adhesion element may be connected to an active output of a power supply, and a ground pad affixed to the patient may be connected to a return terminal of the power supply. The second adhesion element may not be connected to the power supply but may oppose the first adhesion element and compress tissue between the two adhesion elements, promoting heating and adhesion.

The catheters and adhesion elements may be configured to coapt with each other and to compress tissue between the adhesion elements in order to adhere tissue when it is heated. In some instances, a system may comprise first and second catheters each having one or more magnets, such that magnets of the first catheter may be attracted to magnets of the second catheter to bring the catheters in closer approximation. In some variations, the adhesion elements themselves may be magnets and may be configured to be attracted to each other. As such, the adhesion elements may promote axial and/or rotational alignment of the catheters. Additionally or alternatively, the catheters may comprise coaption regions comprising magnets, and/or may comprise one or more visual alignment aids, to promote tissue coaption as well as axial and/or rotational alignment of the catheters. For instance, a rotational indicator may allow catheter alignment to be visualized under fluoroscopy, such that a user may manipulate the catheters into a desired position. In some variations, the catheters may also be configured to promote the ability of an adhesion element to press into tissue, as described in more detail herein. The catheters may have the same configuration of elements, or may have different and/or complementary configurations of elements.

Figure 2D:
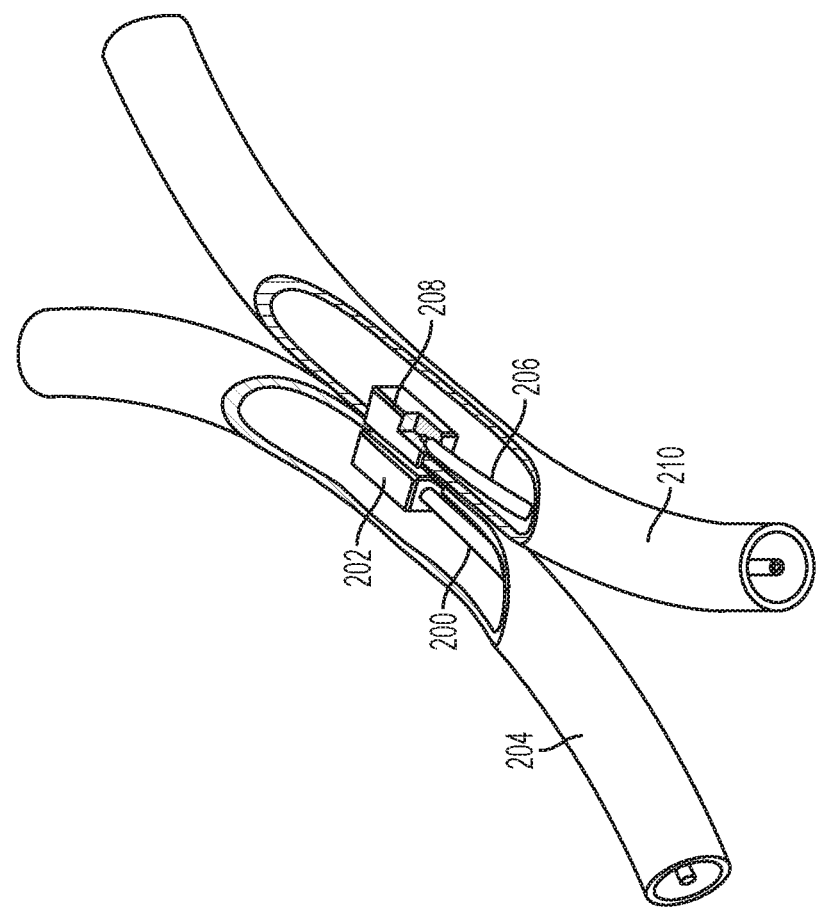
Figure 2C:
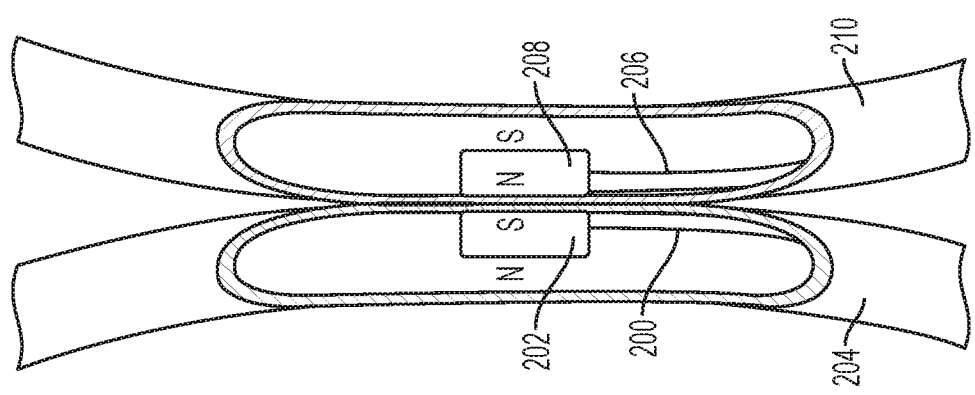

FIGS. 2A-2C show an exemplary system comprising two catheters each comprising an adhesion element comprising a magnet. A first catheter (200) comprising an adhesion element (202) is shown located within a first blood vessel (204). A second catheter (206) comprising an adhesion element (208) is shown located within a second blood vessel (210). The shape and material of the adhesion elements may help to align one catheter in a first vessel with another catheter in a second vessel, and may help to ensure optimal heating and adhesion. In the variation shown in FIGS. 2A-2D, each of the adhesion elements (202, 208) comprises a rectangular magnet. The adhesion elements (202, 208) may be configured to be attracted to each other when in proper axial and rotational alignment. FIGS. 2A-2B show the catheters (200, 206) placed in the vessels without coaption due to magnetic attraction, while FIGS. 2C-2D show the catheters coapted due to magnetic attraction between the adhesion elements (202, 208). When the catheters are coapted as in FIGS. 2C-2D, the walls of vessels (204, 210) may be compressed between the two adhesion elements (202, 208). That is, during alignment of the catheters (200, 206), the attractive magnetic forces of the adhesion elements (202, 208) may bring the catheters (200, 206) and blood vessels (204, 210) into closer approximation, as shown in FIGS. 2C-2D. This compression may aid with heating and adhesion. Each of the adhesion elements (202, 208) may comprise a flat contact surface configured to be contact with the interior vessel wall when the catheters are coapted across the vessel walls.

Figure 3:
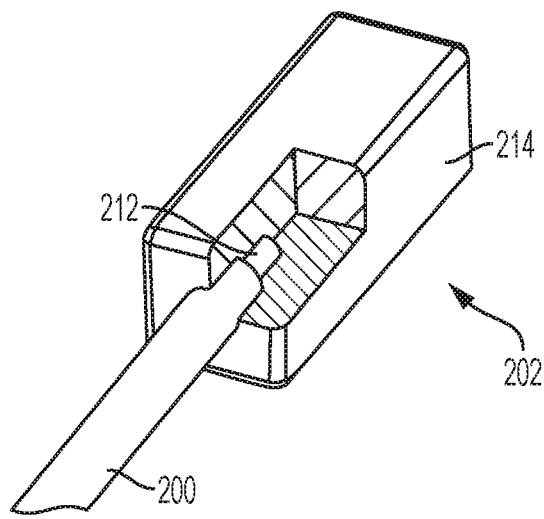
FIGS. 3-4 are perspective views of a distal portion of an illustrative variation of a catheter comprising an adhesion element described here.

The adhesion elements (202, 208) may comprise a conductive material and may be connected to a power supply configured to provide electrical current for heating tissue. FIG. 3 is a perspective view of a distal end of the catheter (200) and the adhesion element (202), shown with a portion of the adhesion element cut away to depict the interior of the adhesion element. As described above, the adhesion element (202) shown may be a magnet that may coapt with another magnet of another catheter (e.g., adhesion element (208) of catheter (206)) to compress tissue therebetween. The adhesion element (202) may comprise one or more flat contact surfaces (214) for providing flush contact with tissue to be heated. Furthermore, in addition to bringing the catheters closer together and compressing tissue, a flat contact surface, such as contact surface (214), may allow a lateral magnetic coaption force to be generated and translated into an aligning torque, which may aid rotational alignment, as well as axial alignment, with an adhesion element of a second catheter. A wire (212) may be located within the catheter (200) and may electrically couple the adhesion element (202) to a power source such as an external power supply. This may allow an external power supply to energize the adhesion element (202). For example, returning to FIGS. 2A-2D, once the adhesion elements (202, 208) are coapted at a desired location, one or more of the adhesion elements may be energized to apply heat to the vessels (204, 210). The heat applied to the compressed vessel tissue (204, 210) may denature proteins in a manner to adhere the vessels together and may form a weld, which may increase the mechanical strength of the vessels. Upon completion of welding between the blood vessels (204, 210), the catheters (200, 206) may be removed.

When heat is applied to the compressed vessels using the devices, systems, and methods described herein, heating tissue to 70° C. may result in denaturation. In some variations, the delivered energy may be constant, while in other variations it may be modulated. In some variations, the tissue may be heated by the delivery of radiofrequency energy to tissue. The power source may deliver energy having any suitable waveform to the tissue via the adhesion elements, such as but not limited to waveform having a sinusoidal or square shape. Electrical energy delivered to tissue may have a peak voltage below the ionization threshold of the tissue. For example, when the waveform is a sinusoidal waveform, the peak voltage may in some variations be below about 150 V. It should also be appreciated that in other variations, current need not travel through tissue in order to heat the tissue. For example, the tissue may be heated through ohmic heating of the adhesion elements. For example, each adhesion element may comprise a resistor resulting in ohmic heating. In these instances, either AC or DC current may be used. In yet other variations, the tissue may be heated through laser or ultrasonic energy delivery.

Figure 4:
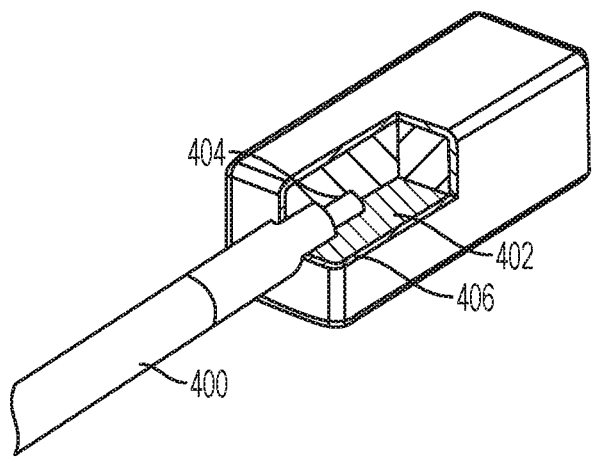

In some variations, one or more surfaces of an adhesion element may be coated with a material that may facilitate removal of the adhesion element from a tissue surface after heating. For example, one or more surfaces of an adhesion element may be coated with one or more layers of PTFE, parylene, silicone, or another fluoropolymer. FIG. 4 is a perspective view of another variation of a catheter (400) comprising an adhesion element (402) comprising a rectangular magnet, and a wire (404) extending through the catheter (400) to electrically couple to the adhesion element (402) to a power supply. A surface of the adhesion element (402) may comprise a coating (406), wherein the coating comprises a material that may facilitate the removal of the adhesion element (402) from a tissue surface without sticking. For example, the coating (406) may comprise one or more layers of PTFE, parylene, silicone, or another fluoropolymer. In some variations, the coating (406) may additionally or alternatively comprise a jacket of material for enhanced biocompatibility or electrical conductivity, such as one or more of gold, platinum, and titanium. In some variations, the adhesion element (402) may be additionally or alternatively partially coated with an insulative coating in order to insulate certain surfaces and leave other surfaces exposed for electrical conduction to the tissue. This may direct and/or isolate energy delivery to a specific region of tissue and/or in a specific shape.

Generally, catheters in the coapted state, as shown in FIGS. 2C-2D for example, may sandwich the tissue interposed between their surfaces with a desired pressure as determined by the size, shape, and material composition of the adhesion elements. Adhesion elements having a flat contact surface, as shown in FIGS. 2A-4 for example, may promote rotational alignment and may better compress tissue for adhesion. These flat surfaces may help to naturally align the adhesion elements with each other, as two flat surfaces may generate a greater aligning torque for a given amount of rotational misalignment than two curved surfaces. For example, in some instances, the aligning torque generated between flat magnetic surfaces at 5 degrees of misalignment is at least approximately 18 times stronger than that of the aligning torque between magnetic cylinders.

FIGS. 5A-5E show a variety of possible shapes for adhesion elements, each comprising a flat contact surface. For example, an adhesion element (500) may have a square cross-section (FIG. 5A); an adhesion element (502) may have a triangular cross-section (FIG. 5B); an adhesion element (504) may have a hexagonal cross-section (FIG. 5C); an adhesion element (506) may have an a rectangular cross-section (FIG. 5D); an adhesion element (508) may have a semi-circular cross-section (FIG. 5E), or the like to provide a flat contact surface for an adhesion element.

Figure 8:
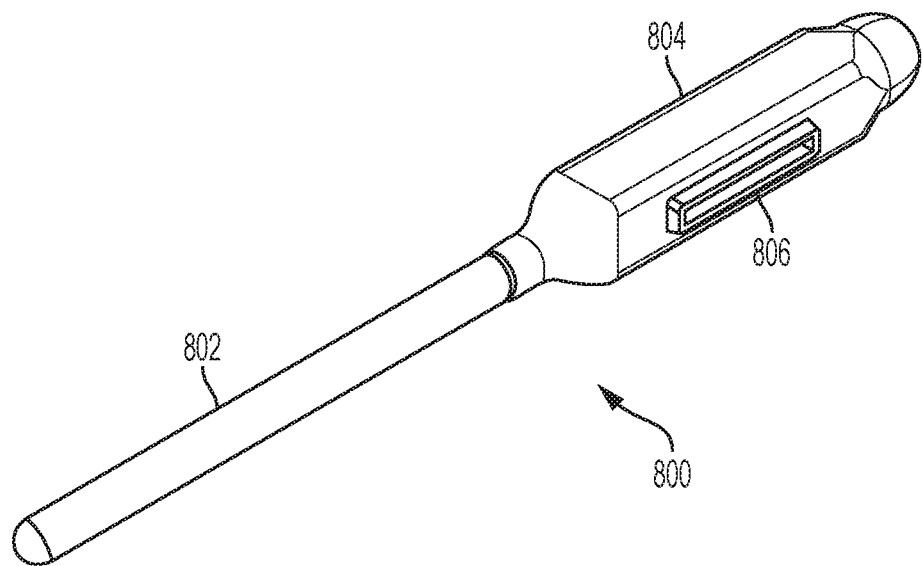

However, in other variations, the adhesion elements may not comprise flat contact surfaces. For example, FIG. 5F illustrates an adhesion element (510) having a circular cross-section. As another example, FIGS. 6A-6B illustrate cross-sectional views of two adhesion element pairs, where one adhesion element is configured to be located in a first tubular structure (e.g., a blood vessel), and a second adhesion element is configured to be located in a second tubular structure (e.g., a second blood vessel). The adhesion elements shown there may comprise one or more protrusions and recesses, where the protrusions and recesses may be complementary. These protrusions and recesses may form an indent in tissue interposed between the adhesion elements. Pairs of adhesion elements having complementary shapes, as shown in FIGS. 6A-6B, may allow greater pressure to be applied to tissue between the two adhesion elements. In some variations, the protrusions (608, 610) may have the shape of a block (see adhesion element (600) in FIG. 6A) or a rigid fin (see adhesion element (604) in FIG. 6B) or point. The recesses (612, 614) of adhesion elements (602, 606) may have complementary shapes to the protrusions (608, 610). In other variations, a pair of adhesion elements may have the same shape. For example, FIG. 6C illustrates a cross-sectional view of a pair of matching adhesion elements (616, 618), each having a raised perimeter and a recessed central region (620, 622). A similar adhesion element having a raised rectangular perimeter and a recessed central region is shown in FIG. 8, described in more detail herein. In some variations, the protruding member may have a hollow interior for decreasing the surface area of the protruding member so that a first current may be applied to adhere tissue and a second current may be supplied to cut an opening through the tissue.

The adhesion elements described herein may be attached to catheters, as shown for example in FIGS. 2A-2D. Generally, the systems may comprise a first catheter for placement in a first tubular structure (e.g., a blood vessel) and a second catheter for placement in a second tubular structure (e.g., a blood vessel), where each catheter may comprise at least one adhesion element. The catheters may have any suitable diameter. For intravascular use, for example, the catheters may be about 4 French, about 5.7 French, about 6.1 French, about 7 French, about 8.3 French, between about 4 French and about 9 French, between about 4 French and about 7 French, between about 4 French and about 6 French, or the like. In the variation shown in FIGS. 2A-2D, the widest dimension of the adhesion elements (202, 208) is greater than the diameter of the catheters (200, 206). This may allow the contact surfaces of the adhesion elements (202, 208) to more easily contact tissue.

Figure 7:
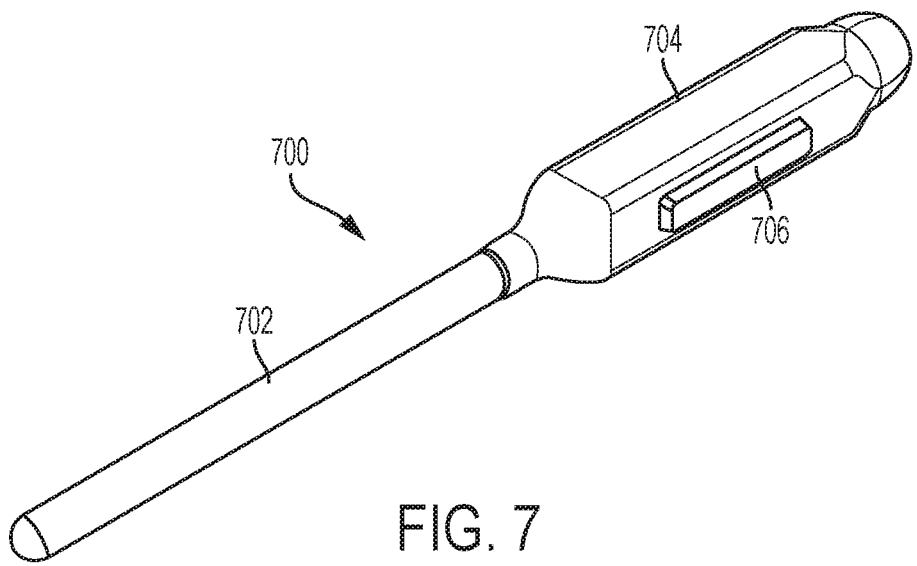
FIGS. 7-8 are perspective views of distal portions of variations of catheters comprising adhesion elements described here.

In other variations, the catheters described herein may be configured to promote the ability of an adhesion element to press into tissue. For example, the adhesion element may be located on a portion of a catheter having a greater diameter than an adjacent portion of a catheter. This may allow the contact surfaces of the adhesion elements to more easily contact tissue. For example, FIG. 7 is a perspective view of a variation of a catheter (700) having an adhesion element (706) embedded within a portion of the catheter and having an exposed flat contact surface. Catheter (700) comprises a proximal portion (702), a distal portion (704), and an adhesion element (706) disposed on the distal portion (704) and having a flat contact surface. As shown, the largest cross-sectional dimension of the distal portion (704) comprising the adhesion element (706) is larger than the largest cross-sectional dimension of the proximal portion (702) of the catheter. As such, the adhesion element (706) may be able to press into tissue without obstruction from contact between the proximal portion (702) of the catheter (700) and tissue, for example, a vessel wall. FIG. 8 illustrates another catheter (800) comprising a proximal portion (802) and a distal portion (804), where the distal portion (804) has a larger cross-sectional dimension than the proximal portion (802). The catheter (800) further comprises an adhesion element (806) disposed on the distal portion (804), where the adhesion element (806) comprises a raised perimeter with a central rectangular recess. That is, the adhesion element (806) may define an opening such that, for example, tissue indented against the adhesion element (806) forms a rectangular indent around the perimeter formed by the raised portion of the adhesion element (806). Energy may be supplied to activate the adhesion element (806) to adhere two vessels together. In some variations, an opposing adhesion element on a second catheter may be configured to fit within the central rectangular recess, which may allow for increased pressure application to tissue located between the adhesion element (806) and the opposing adhesion element.

Figure 9A:
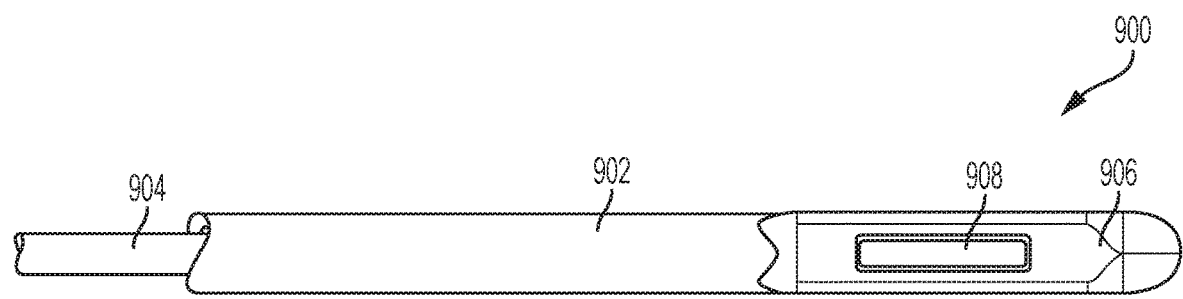
FIGS. 9A-9E are side views (FIGS. 9A, 9B, 9D) and perspective views (FIGS. 9C, 9E) of distal portions of a catheter in retracted (FIGS. 9A-9C) and extended (FIGS. 9D-9E) configurations.
Figure 9B:
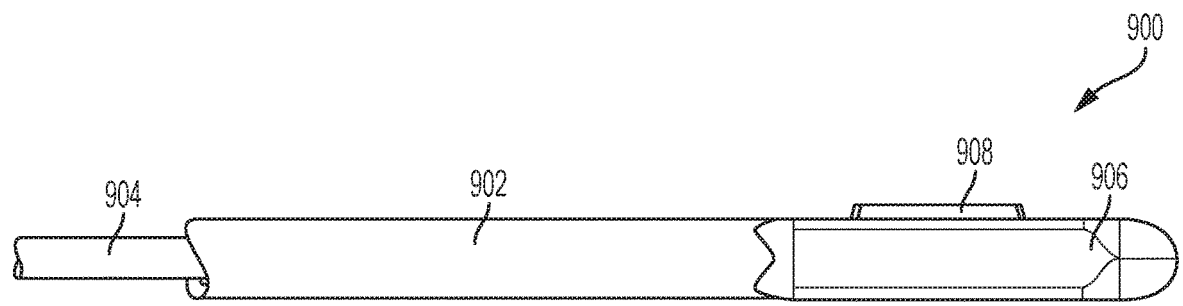
Figure 9C:
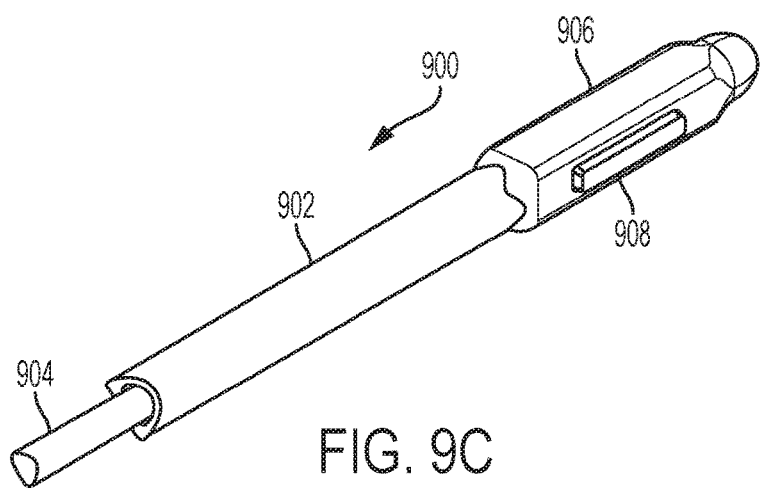
Figure 9D:
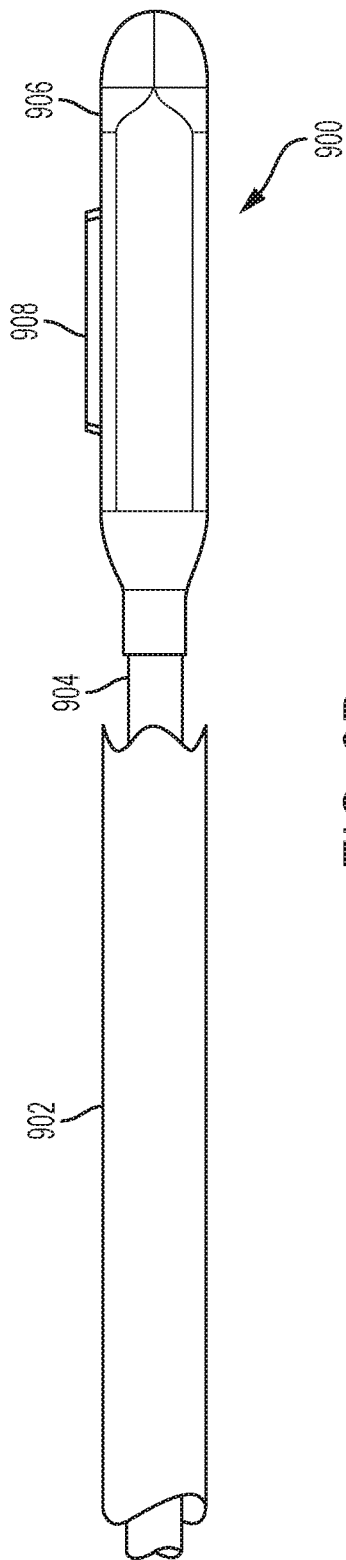
Figure 9E:
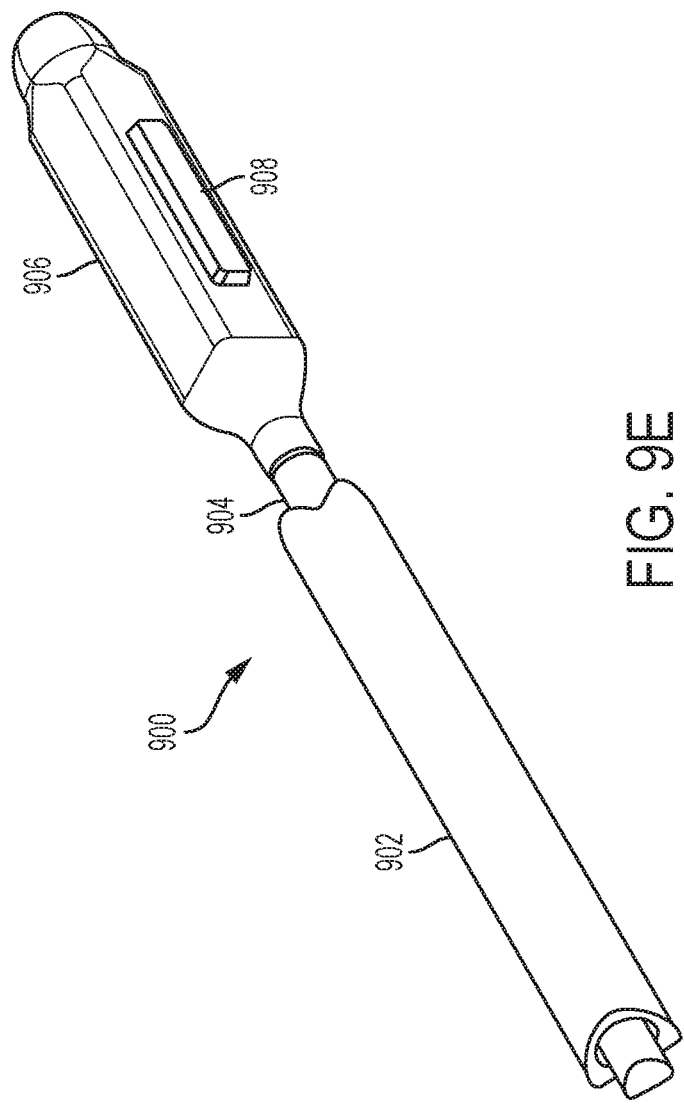

In some variations, the catheters described herein may be configured to have adjustable stiffness, for example in the event that an increase in pushability, flexibility, or torquability may be desired. For example, FIGS. 9A-9E show side and perspective views of variations of a catheter (900) similar to catheter (700) comprising a proximal portion (904) and a distal portion (906) comprising an adhesion element (908) having a flat contact surface. The distal portion (906) may be fixedly connected to an inner proximal portion (904) and may have a larger cross-sectional dimension than the inner proximal portion (904). The inner proximal portion (904) may be slidable within an outer proximal portion (902), where the outer proximal portion comprises a tubular shape. As such, the distal portion (906) and part of the inner proximal portion (904) may be configured to extend distally from the outer proximal portion (902) between a retracted position (FIGS. 9A-9C) and an extended configuration (FIGS. 9D-9E). In the extended configuration shown in FIGS. 9D-9E, the distal portion (906) of the catheter (900) may have increased ability to deform and/or press into tissue when the adhesion element (908) is attracted to a corresponding adhesion element of another catheter, since deformation of the inner proximal portion (904) is not limited by the outer proximal portion (902). In the retracted configuration shown in FIGS. 9A-9C, the distal portion (906) of the catheter (900) may have increased pushability, since deformation of the inner proximal portion (904) is limited by the outer proximal portion (902). In this way, either of the extended or retracted configurations (or an intermediate configuration between the extended or retracted configurations) may be selected based on one more requirements related to pushability, flexibility, and/or torquability.

In FIGS. 2A-4 and 7-9E, the adhesion elements are shown at or near a distal end of the catheters. However, it should be appreciated that adhesion elements may be located along any suitable portion of the catheters described herein (e.g., a distal end, an intermediate portion, or combinations thereof). It should also be appreciated that a catheter may have any suitable number (e.g., zero, one, two, three, or four or more) and combination of adhesion elements. In variations in which a catheter comprises two or more adhesion elements, multiple adhesion elements may be used to create multiple adhesion regions, either simultaneously or sequentially. In other variations, multiple adhesion elements may interact to form a single adhesion region.

Figure 10:
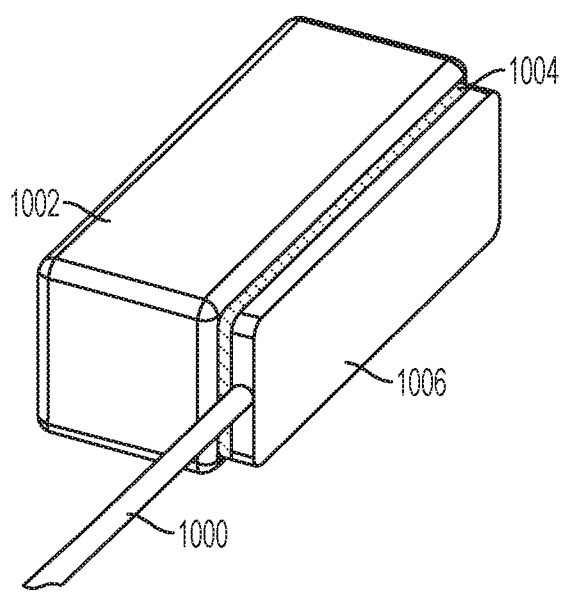
FIG. 10 is a perspective view of an illustrative variation of a distal portion of a catheter comprising a separate magnet and adhesion element.

Furthermore, in other variations, an adhesion element need not comprise a magnet. While magnetic adhesion elements may help to compress tissue between two catheters, in some variations the adhesion elements may comprise any material suitable for heating tissue to cause adhesion. For example, the adhesion elements may comprise any suitable conductive material. In some of these variations, the catheters described herein may comprise one or more adhesion elements and one or more separate alignment features to assist in coaption and rotational and/or axial alignment of the catheters relative to each other. In some of these variations, alignment features may assist a user in manual positioning of the catheters. Generally, in these variations, the catheters may comprise at least one of a flat coaption surface, a magnet, and a rotational indicator. Combinations of one or more of these elements may improve the ability of a user to orient and align catheters rotationally. For instance, the catheters described herein may comprise one or more adhesion elements and a separate coaption region comprising one or more magnets to promote coaption and alignment. For example, a catheter may comprise a magnet and a separate adhesion element comprising an electrode. FIG. 10 is a perspective view of such a variation of a catheter (1000) comprising a magnet (1002) and a separate electrode (1006). The magnet (1002) may be separated from the electrode (1006) by an electrical and/or thermal insulator (1004). The thermal insulator may comprise, for example, polyimide, PEEK, PTFE, and/or ceramic. In this configuration, the magnet (1002) may act to promote tissue compression between the flat contact surface of the adhesion element (electrode (1006)) and an adhesion element in an adjacent vessel and may promote proper alignment between the adhesion elements, while the electrode (1006) may act as the adhesion element. In other variations, the electrode (1006) may be disposed directly on the magnet (1002).

Figures 11A, 11B:
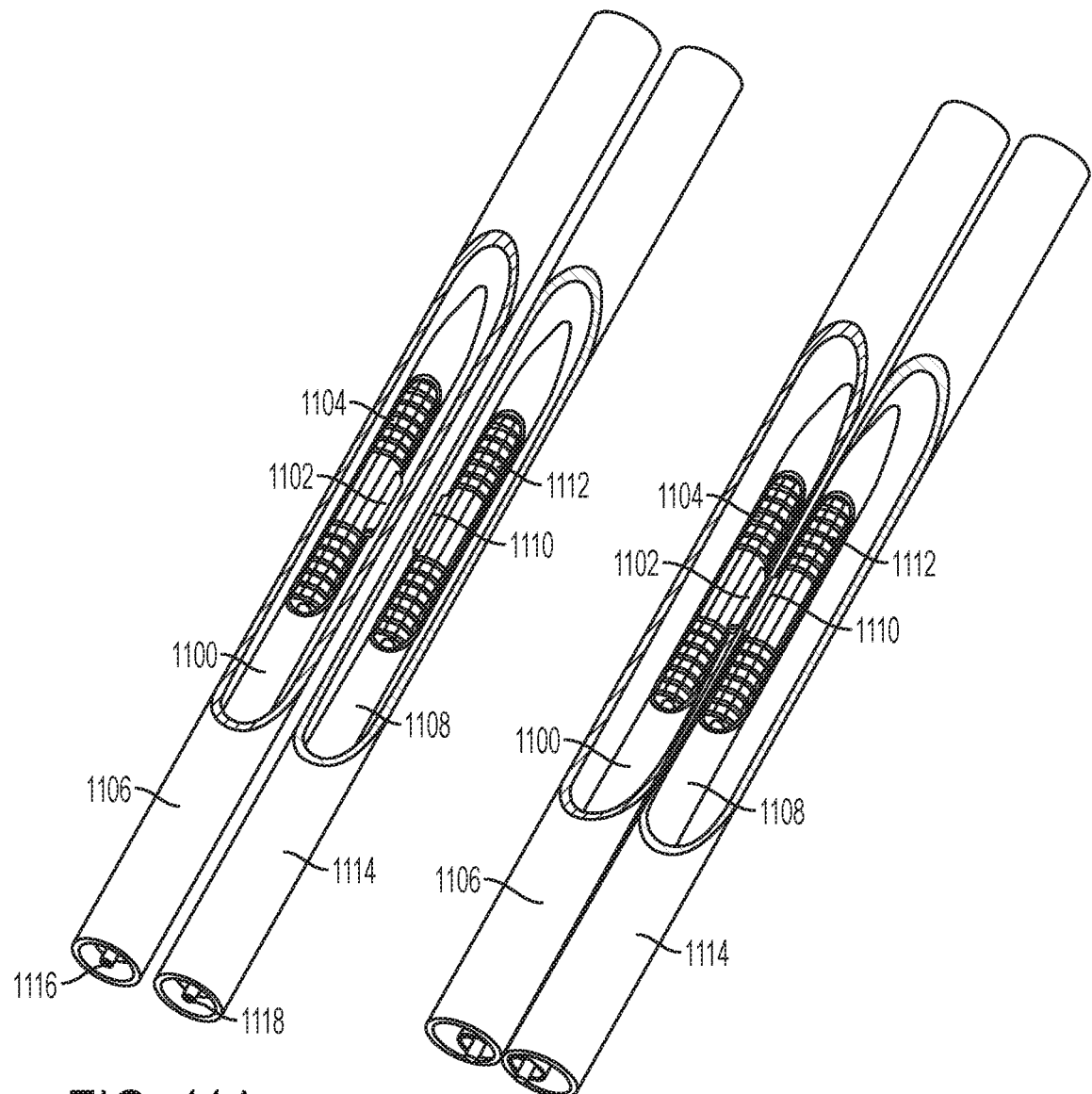
FIGS. 11A-11B are perspective views of an illustrative variation of a system described here.

FIGS. 11A-11B illustrate another variation of a system in vasculature comprising a first catheter (1100) in a first blood vessel (1106) and a second catheter (1108) in a second blood vessel (1114). The first catheter (1100) may comprise a first adhesion element (1102) that may be a non-magnetic adhesion element, such as a non-magnetic electrode, and the second catheter (1108) may comprise a second adhesion element (1110) that may be non-magnetic adhesion element, such as a non-magnetic electrode. It should be appreciated that in other variations, the first and second adhesion elements (1102, 1110) may comprise magnetic electrodes. The adhesion elements (1102, 1110) may be connected via electrical leads (1116, 1118) to a power source (not shown), as described in more detail herein. The first catheter (1100) may further comprise a first coaption region (1104) comprising one or more magnets that may be distal and proximal to the first adhesion element (1102). The second catheter (1108) may further comprise a second coaption region (1112) comprising one or more magnets that may be distal and proximal to the second adhesion element (1110). Generally, the magnets may be configured to be attracted to one or more magnetic fields (e.g., produced by one or more magnets of the other catheter). The magnets may help to align or otherwise reposition the catheters (1000, 1108) when placed in the vasculature. Once the first and second catheters (1000, 1108) have been positioned, the attractive magnetic forces may also act to maintain the relative positions of the catheters (1000, 1108). When the first and second catheters (1000, 1108) are placed in respective blood vessels (1106, 1114), tissue positioned between the blood vessels and/or limited compliance of the blood vessels may limit the extent to which the magnets of the first and second catheters bring the first and second catheters toward each other. The magnets may additionally or alternatively help to ensure that the catheters (1000, 1108) are in proper axial and/or rotational alignment relative to each other. Such axial and/or rotational alignment of the catheters (1000, 1108) may also facilitate alignment of the adhesion elements (1102, 1110) relative to a target location for vessel adhesion.

It should be appreciated that the catheters of the systems described here may comprise one or more magnets, and each catheter may comprise any number of individual magnets (e.g., one, two, three, four, five, six, seven, or eight or more, etc.). In some variations in which a catheter comprises multiple magnets, one or more magnets may act as adhesion elements and be configured to heat tissue (e.g., through delivery of electrical current), while one or more other magnets may not be configured to heat tissue. In variations in which a catheter comprises a plurality of magnets, these magnets may be grouped into one or more magnet arrays. The magnets may be located inside and/or outside of a catheter body. The magnets may be positioned at any suitable location along the length of the catheter. Generally, the dimensions of the magnets described herein may be selected based on the size of the catheters carrying the magnets, which in turn may be selected based on the anatomical dimensions of the blood vessels through which the catheters may be advanced. For example, if the catheter is to be advanced through a blood vessel having an internal diameter of about 3 mm, it may be desirable to configure any magnet to be less than about 3 mm at the widest part of its cross-section, to reduce the risk of injury to vessel walls during advancement and manipulation of the catheter. Each magnet may have any suitable length (e.g., about 5 mm, about 10 mm, about 15 mm, about 20 mm, or the like), although it should be appreciated that in some instances longer magnets may limit the flexibility of the catheter to maneuver through tissue.

The magnets described here throughout may be permanent magnets comprising one or more hard magnetic materials, such as but not limited to alloys of rare earth elements (e.g., samarium-cobalt magnets or neodymium magnets, such as N52 magnets) or alnico. In some variations, the magnets may comprise anisotropic magnets; in other variations, the magnets may comprise isotropic magnetics. In some variations, the magnets may be formed from compressed powder. In some variations, a portion of the magnets (e.g., a permeable backing) may comprise one or more soft magnetic materials, such as but not limited to iron, cobalt, nickel, or ferrite. When the magnets are configured to deliver electrical current to tissue, the magnets may comprise conductive material and/or comprise a conductive coating. When the magnets are located within the catheter, as in FIGS. 11A-11B for example, given the limitations on magnet size, it may be desirable in some instances to use magnets configured to produce magnetic fields that increase the magnetic force that can be generated with a magnet of a given size. For example, in some variations the system may comprise one or more of the magnets described in U.S. patent application Ser. No. 14/214,503, filed on Mar. 14, 2014, and titled "FISTULA FORMULATION DEVICES AND METHODS THEREFOR," and/or U.S. patent application Ser. No. 14/657,997, filed on Mar. 13, 2015, and titled "FISTULA FORMATION DEVICES AND METHODS THEREFOR," each of which is hereby incorporated by reference in its entirety.

It should be appreciated that while some of the systems described here comprise a first catheter and a second catheter each comprising one or more permanent magnets (which may or may not be configured to heat tissue), in other variations either the first or second catheter may comprise ferromagnetic elements (i.e., elements attracted to but not generating a permanent magnetic field). For example, in some variations, the first catheter may include only one or more ferromagnetic elements while the second catheter comprises one or more permanent magnets. In other variations, the second catheter may include only one or more ferromagnetic elements while the first catheter comprises one or more permanent magnets. However, in other variations, one or both of the first and second catheters may include any suitable combination of ferromagnetic, permanent, and/or other suitable kinds of magnets.

Returning to FIG. 11A-11B, these figures illustrate the catheters (1100, 1108) advanced through respective vessels (1106, 1114). When the catheters (1100, 1108) are brought together, the attractive magnetic forces of the magnets within the coaption regions (1104, 1112) may bring the catheters (1100, 1108) and blood vessels (1106, 1114) in closer approximation, as shown in FIG. 11B. In variations where the adhesion elements are magnetic, the adhesion elements may also bring the catheters together. One or more of the adhesion elements (1102, 1108) may then be energized so as to apply heat to the vessels, as described in more detail herein.

The systems described herein may further comprise one or more additional alignment features to help ensure that the catheters are axially and/or rotationally aligned prior to heating the tissue to achieve adhesion. For example, one or both of the first and second catheters may comprise a visual alignment aid for indirectly visualizing the alignment of a catheter within a tubular structure or relative to another catheter, such as via fluoroscopy, during positioning and/or alignment thereof.

In some variations, the visual alignment aid may comprise a rotational indicator. A rotational indicator may serve as a visual marker for guiding rotational alignment of two catheters as viewed under fluoroscopy. The rotational indicators of each catheter may be used to rotationally and/or axially position the catheters such that that one or more adhesion elements are properly positioned to adhere tissue. Generally, a rotational indicator may be configured such that its rotational orientation is discernable in a two-dimensional fluoroscopic image. A rotational indicator may comprise a radiopaque portion. The first catheter may include a first radiopaque portion and the second catheter may include a corresponding second radiopaque portion. An X-ray beam may fluoroscopically image an orientation of the first radiopaque portion and the second radiopaque portion, and the image may be shown on a display for a user. The user may then manipulate one or both of the catheters to align the catheters. A rotational indicator may be provided along any suitable portion of the catheter. In some variations, the rotational indicator may comprise any radiopaque metal, such as tungsten, platinum iridium, stainless steel, titanium, as well as a tungsten filled polymer, zirconia ceramic, or any suitable radiopaque material. In some variations, the rotational indicator may comprise a radiopaque film Rotational indicators suitable for use in the catheters described herein are discussed in more detail in U.S. patent application Ser. No. 15/406,755, filed Jan. 15, 2017, titled "DEVICES AND METHODS FOR FORMING A FISTULA" and claiming the benefit of U.S. Provisional Application No. 62/399,471, filed Sep. 25, 2016, and U.S. Provisional Application No.

62/279,603, filed Jan. 15, 2016, which is hereby incorporated by reference in its entirety.

II. Methods

Also described here are methods for adhering tissue of two tubular structures, such as two blood vessels. When the tubular structures comprise blood vessels, the two blood vessels may be two closely-associated blood vessels, such as a vein and an artery, two veins, two arteries, or the like. Generally, when the tubular structures are blood vessels, the methods described here comprise accessing a first blood vessel with a first catheter having features as described herein, and advancing the first catheter to a target location within the first blood vessel. A second blood vessel may be accessed with a second catheter having features as described herein, and the second catheter may be advanced to a target location within the second vessel. After the vessels are brought toward each other and aligned, one or more adhesion elements may be activated to heat and denature tissue to fuse tissue together and form an adhesion between the two vessels. The catheters may then be removed. In some variations, a fistula may be formed through a portion of the welded tissue. In some instances, a fistula may be formed using the devices, systems, and methods in U.S. patent application Ser. No. 13/298,169, filed on Nov. 16, 2011, and titled "DEVICES AND METHODS FOR FORMING A FISTULA," which is hereby incorporated by reference in its entirety, and in U.S. patent application Ser. No. 15/406,755, filed Jan. 15, 2017, titled "DEVICES AND METHODS FOR FORMING A FISTULA" and claiming the benefit of U.S. Provisional Application No. 62/399,471, filed Sep. 25, 2016, and U.S. Provisional Application No. 62/279,603, filed Jan. 15, 2016, which was previously incorporated by reference in its entirety, while in other variations, the devices and systems described herein may be used to form a fistula.

When the tubular structures are blood vessels, advancement of one or more catheters through a vessel to a target site is not particularly limited. In some variations, a first catheter is advanced into an artery, and a second catheter is advanced into a vein. In other variations, a first catheter is advanced into a first vein, and a second catheter is advanced into a second vein. In still other variations, a first catheter is advanced into a first artery and a second catheter is advanced into a second artery. In some variations, a first catheter is advanced into a vein, and the second catheter is advanced into an artery. The first and/or second catheters may be advanced over a guidewire or in any suitable manner and may or may not occur under indirect visualization (e.g., via fluoroscopy, X-ray, or ultrasound).

In some variations, each of the first or second catheters may comprise one or more adhesion elements as described herein. The adhesion elements may or may not be magnetic. In some variations, aligning the first and second catheters may comprise axial and/or rotational alignment of the adhesion elements. In variations where both the first and second catheters comprise adhesion elements, the catheters may be oriented to align these adhesion elements. The catheters may be aligned in any suitable manner. In some variations, magnetic adhesion elements may generate an attractive force between the first and second catheters, which may pull the catheters toward each other. In these or other variations, separate coaption regions may comprise one or more magnets configured to generate an attracted force between the first and second catheters.

Additionally or alternatively, the catheter systems described herein may comprise one or more rotational indicators allowing for indirect visualization of catheter alignment such as through fluoroscopy. In variations where the first and/or second catheters comprise one or more rotational indicators, such as those described herein, the markers may be viewed (e.g., via fluoroscopy, X-ray, or the like) to ensure that the catheters have the proper axial and/or radial orientation relative to each other. For example, the catheter and rotational indicators may be visualized fluoroscopically during alignment of the catheters, and in some cases from at least advancement steps through alignment of the catheters. The user may view the rotational indicators in a fluoroscopic image to determine a rotational alignment of the catheters and may rotate the catheters until alignment is achieved. When the catheters are viewed as axially aligned based on the position of the rotational indicators or another portion of the catheters, the user may bring the catheters into close approximation.

Figure 12A:
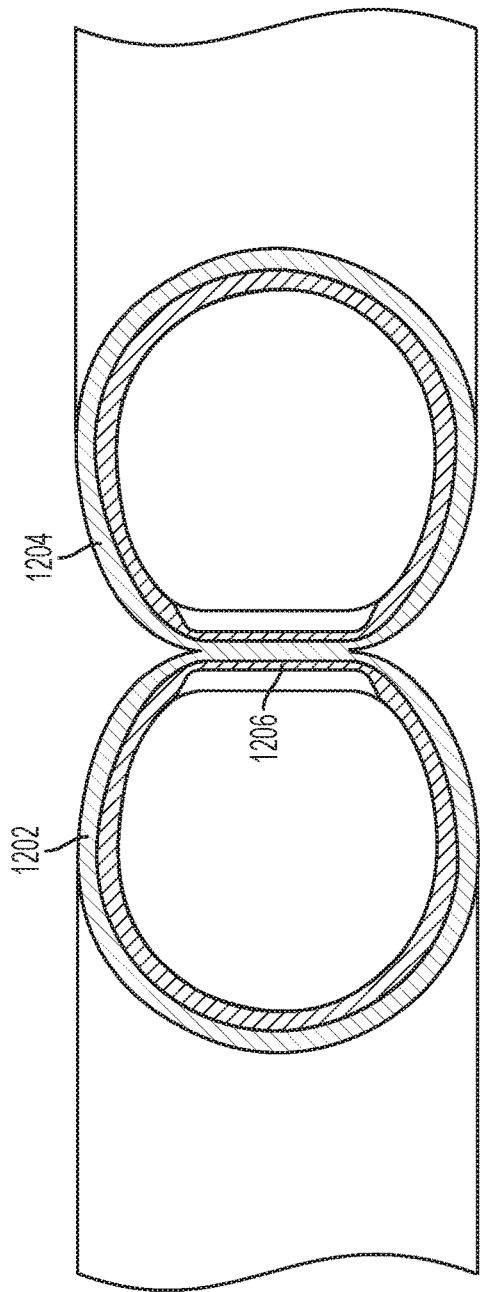
FIGS. 12A-12B are cross-sectional and plan views, respectively, of adhered vessels.
Figure 12B:
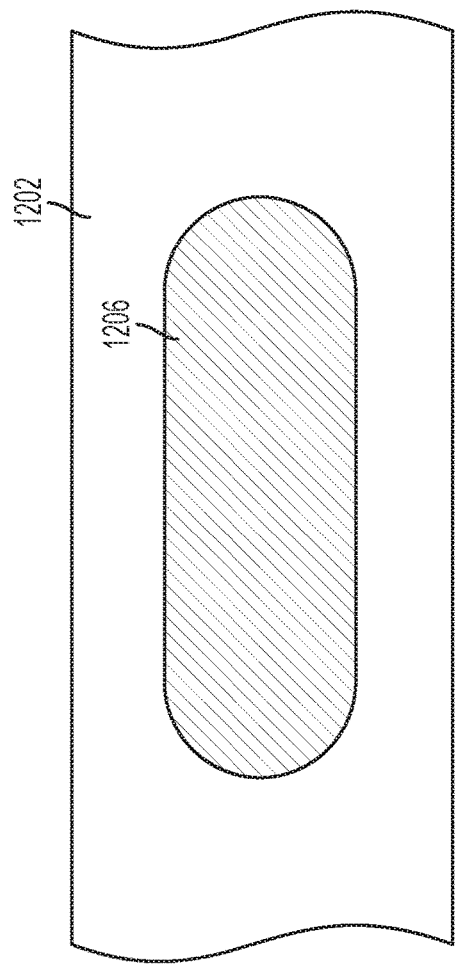

Once the catheters are aligned, one or more adhesion elements may be activated to adhere tissue in vessels. As shown in FIG. 12A, one or more adhesion elements may form a thermal weld (1206) between a first vessel (1202) and a second vessel (1204). FIG. 12B is a plan view of the vessel (1202) having a formed weld (1206) in the shape of the adhesion element in contact with the vessel (1202). In some instances, tissue may be heated to form a thermal weld between the intimal, medial, and/or adventitia of the vessels (1202, 1204). The weld (1206) may form a hermetic seal between the vessels, thereby preventing pressurized fluid from ingress or egress through the weld plane. The weld may also be strong enough to prevent the vessels from being pulled apart under forces that may be applied due to bodily function or motion. In other instances, the weld (1206) may be able to withstand internal hydraulic pressure from dissecting the vessels apart, as discussed in further detail herein. In some variations, the weld may have a width of about 0.1 mm to about 15 mm and a length ranging from about 0.1 mm to about 10 cm, although the weld length may vary from this range. In some variations, a plurality of discrete welds may be produced by a single catheter system using a plurality of adhesion elements.

The adhesion elements may adhere tissue by heating the tissue. In some variations, the adhesion elements may heat tissue by delivering radiofrequency energy. In other variations, the adhesion elements may be heated through ohmic heating, which may in turn heat tissue. In yet other variations, the adhesion elements may deliver laser energy to heat tissue, or may deliver ultrasonic energy to heat tissue.

In some variations, the systems discussed herein may comprise an electrosurgical controller coupled to one or more adhesion elements for controlling tissue adhesion. A controller may control the energy delivery to one more adhesion elements to heat tissue based on the selected adhesion parameters. Adhesion parameters may include an energy waveform shape, frequency, amplitude, duration, and so forth. For example, in one non-limiting variation, a controller may be configured to deliver a waveform having a frequency between about 300 kHz and about 500 kHz, with a peak voltage of between about 120 V and about 140 V. In some variations, a controller may be configured to deliver a waveform having a frequency of about 400 kHz, with a peak voltage of about 130 V. The waveform may have any suitable shape, such as a sinusoidal or square shape. The controller may modulate one or more parameters to achieve a desired heating profile. For example, the controller may modulate one or more of the peak voltage or duty cycle of the waveform. In some variations, the electrosurgical controller may deliver energy for a predetermined duration to achieve the intended adhesion. In other variations, the strength of an adhesion cycle may be limited in power and/or duration so as to perform a plurality of adhesion cycles. In this manner, the thermal effects of heating may be dispersed over a longer period of time so as to limit collateral thermal injury to the vessel.

In some variations, tissue parameters may be measured and analyzed in order to determine one or more adhesion parameters. The electrosurgical controller may in some instances monitor the impedance during energy delivery to determine a rate of tissue heating. In other instances, termination of adhesion may occur after measuring a predetermined impedance or a predetermined rate of change of impedance. In order to measure impedance, the system may comprise an impedance metering circuit such as a bipolar sensing circuit with each adhesion element serving as an element. To measure impedance, low power DC or alternating voltage may be applied to the adhesion elements. The resulting current and/or phase may then be measured to determine impedance. Additionally or alternatively, impedance may also be measured during a thermal adhesion period by measuring the impedance in a bipolar or monopolar circuit. In this manner, a single heating cycle may be performed without interrupting the energy delivery cycle to measure impedance. Impedances measured before, after, and/or during an adhesion sequence may determine the level of vessel modification provided. Additionally or alternatively, a catheter may further comprise a thermocouple or thermistor to monitor tissue temperature as an additional input signal for controlling adhesion by the electrosurgical controller. In some variations, one or more impedance measurements or tissue temperature measurements may be outputted to a user as one or more of visual and audio feedback. For example, the system may output an impedance value on a display meter coupled to the catheters. Impedance values may be output as audio tones. In other variations, impedance measurements or tissue temperature information may be provided to the electrosurgical controller to automatically adjust or stop current delivery. For example, tissue measurements indicating that the temperature has reached 70° C. may indicate that protein denaturation has been achieved.

After tissue adhesion is performed using one or more adhesion elements, in some variations a fenestration between the two tubular structures may optionally be formed. In some variations, a fenestration may be formed using different devices, such as a different catheter system. For example, a fistula between the two vessels may be formed using a system and method as described in U.S. patent application Ser. No. 13/298,169, filed on Nov. 16, 2011, and titled "DEVICES AND METHODS FOR FORMING A FISTULA," and in U.S. patent application Ser. No. 15/406,755, filed Jan. 15, 2017, titled "DEVICES AND METHODS FOR FORMING A FISTULA" and claiming the benefit of U.S. Provisional Application No. 62/399,471, filed Sep. 25, 2016, and U.S. Provisional Application No. 62/279,603, filed Jan. 15, 2016, each of which was previously incorporated by reference in its entirety. For example, a fistula may be formed using a system comprising a first catheter and a second catheter. The first catheter may comprise a catheter body, one or more magnetic elements, and a fistula-forming element. The second catheter may comprise a catheter body, one or more magnetic elements, and may optionally comprise a fistula-forming element. In some variations, the fistula-forming element may comprise an electrode configured to move between a low-profile configuration and an extended configuration in which it extends radially away from the catheter body. In some variations the fistula-forming element may be spring-biased toward the extended configuration, i.e., may be configured to self-expand from the low-profile to the extended configuration, and may be held in the low-profile configuration during placement, for example by an external radially inward force on the electrode from a the catheter body or a vessel wall during delivery.

In other variations, a fenestration may be formed using the same catheters but using a separate fistula-forming element. For example, the separate fistula-forming element may be axially displaced along the catheter from the adhesion element, or as another example, a separate fistula-forming element may be located within an adhesion element. In the case of a fistula formed between blood vessels, hemostasis may be created without the need for a separate device or structure (e.g., a suture, stent, shunt, or the like) connecting or joining the blood vessels. In yet other variations, a fenestration may be formed by further activating the adhesion elements to bore through, perforate, or otherwise create a passageway between the two structures (e.g., blood vessels such that blood may flow directly between the two adjoining blood vessels). In some variations in which a fenestration is formed, a first current may be applied to the adhesion element to adhere tissue together while a second current may be applied to form an opening through the tissue in the shape of the adhesion element. For example, the waveform may be modified to have an increased peak voltage. For example, the peak voltage may be increased to reach an ionization threshold. In one non-limiting example, the peak voltage may be increased to about 180 V. In other variations, energy supplied to an adhesion element for a first time period may adhere the two vessels together while continued heating for a second time period beyond the first time period may form a fistula. In one non-limiting example, the first time period may be up to about 10 seconds, while the second time period may be up to an additional about 5 seconds.

Figure 13A:
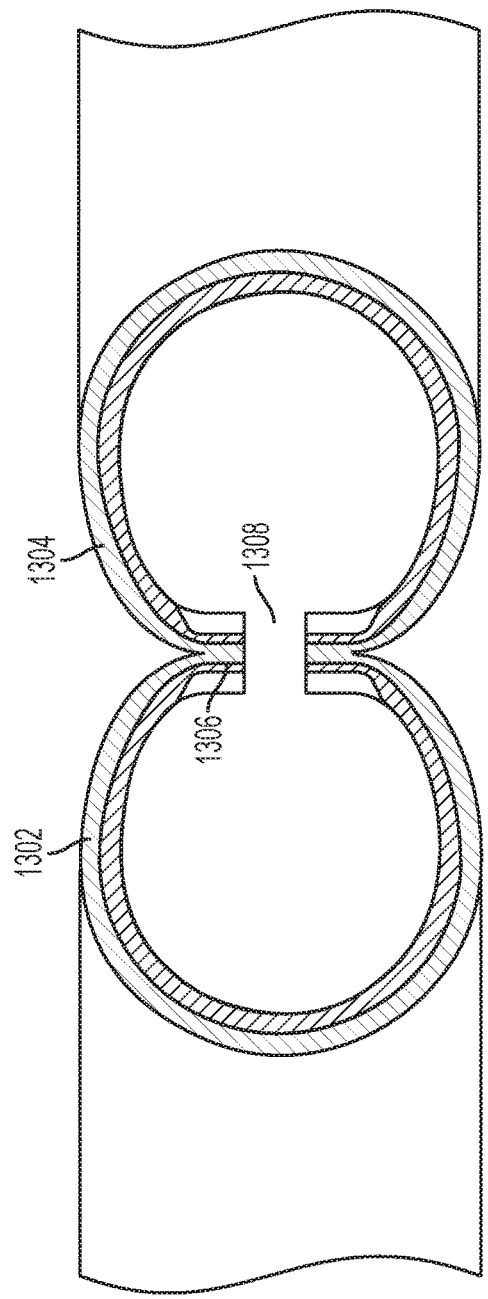
FIGS. 13A-13B are cross-sectional and plan views of a vessel comprising a weld and a fistula.
Figure 13B:
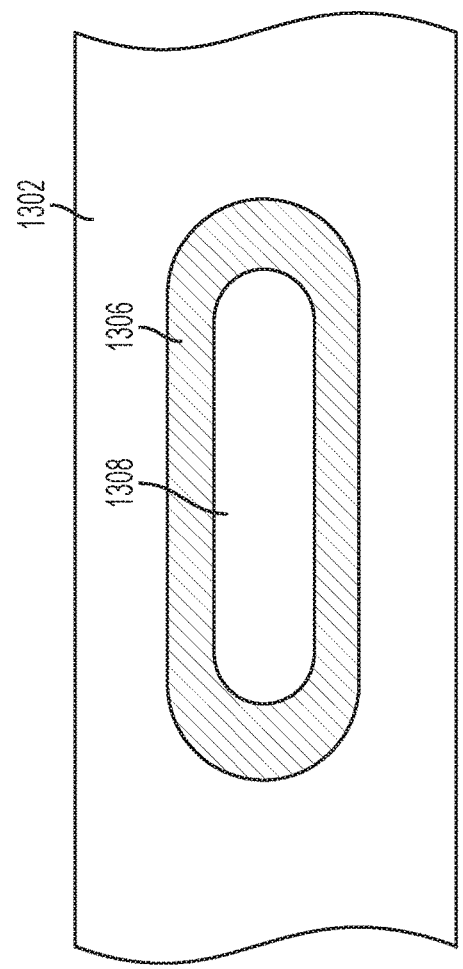

In variations in which a fistula is formed between the two vessels after adhesion, the weld may maintain adhesion of the two attached vessels when the fistula is subsequently formed in the weld. In other words, a weld may prevent pressurized fluids traveling through the fistula from breaching the hermetic seal. In this way, the weld may prevent extravasation or leaking of fluids and thus may provide an enhanced fistula. FIG. 13A shows a cross-sectional view of a thermal weld (1306) surrounding a fistula (1308) between a first vessel (1302) and a second vessel (1304). FIG. 13B shows a plan view of the vessel (1302) and weld (1306) and a fistula (1308) formed therethrough to provide fluid communication through the fistula (1308) while maintaining a perimeter of welded tissue (1306) to prevent fluid leakage.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices and methods described herein may be used in any appropriate combination. The description of certain elements or characteristics with respect to a specific figure are not intended to be limiting or nor should they be interpreted to suggest that the element cannot be used in combination with any of the other described elements.

We claim:

1. A system for adhering two tubular structures together, comprising:

a first catheter comprising a first adhesion element embedded within a portion of the first catheter, wherein the first adhesion element is magnetic and comprises a flat, magnetic contact surface;

a second catheter comprising a second adhesion element embedded within a portion of the second catheter, wherein the second adhesion element is magnetic and comprises a flat, magnetic contact surface, wherein each of the first and second adhesion elements comprises a resistor for ohmic heating; and a power source connected to the resistor of the first and second adhesion elements, wherein the flat, magnetic contact surfaces are heated in response to heating the resistor to a temperature sufficient to form a thermal weld between the two tubular structures via the flat, magnetic contact surfaces of the first adhesion element and the second adhesion element, the thermal weld providing a hermetic seal preventing egress of a fluid through a thermal weld plane;

wherein the first catheter comprises a proximal portion and a distal portion, wherein the largest cross-sectional dimension of the distal portion is larger than the largest cross-sectional dimension of the proximal portion, and wherein the first adhesion element is located on the distal portion; wherein the second catheter comprises a second proximal portion and a second distal portion, wherein the largest cross-sectional dimension of the second distal portion is larger than the largest cross-sectional dimension of the second proximal portion, and wherein the second adhesion element is located on the second distal portion.

2. The system of claim 1, wherein the first adhesion element is located at a distal end of the first catheter, and the second adhesion element is located at a distal end of the second catheter.

3. The system of claim 1, wherein the first adhesion element is coated with one or more layers of a fluoropolymer.

4. The system of claim 1, wherein at least one of the pushability, flexibility, or torquability of the first catheter is adjustable.

5. The system of claim 1, wherein the first catheter comprises a distal portion, an inner proximal portion, and an outer proximal portion.

6. The system of claim 5, wherein the outer proximal portion is slidable relative to the distal portion.

7. The system of claim 6, wherein the distal portion is configured to extend away from the outer proximal portion when moved from a retracted configuration to an extended configuration.

8. The system of claim 1, further comprising a rotational indicator.

9. The system of claim 1, wherein the first adhesion element defines a recess.

10. The system of claim 1, wherein the power source comprises a controller configured to control energy delivery to the catheters.

11. The system of claim 10, wherein the controller is configured to:

supply a first current to the resistor for forming the thermal weld; and supply a second current to the resistor for forming a fenestration within the thermal weld.

12. The system of claim 1, wherein the first adhesion element has a square cross section.

13. The system of claim 1, wherein the first adhesion element has a triangular cross section.

14. The system of claim 1, wherein the first adhesion element has a hexagonal cross section.

15. The system of claim 1, wherein the first adhesion element has a rectangular cross section.

16. The system of claim 1, wherein the first adhesion element has a semi-circular cross section.

* * * * *